United States Patent [19]
Linkous

[11] Patent Number: 5,518,992
[45] Date of Patent: May 21, 1996

[54] PHOTOCATALYTIC SURFACING AGENTS FOR INHIBITING ALGAE GROWTH

[75] Inventor: Clovis A. Linkous, Merritt Island, Fla.

[73] Assignee: University of Central Florida, Orlando, Fla.

[21] Appl. No.: 286,656

[22] Filed: Aug. 5, 1994

[51] Int. Cl.$^6$ .......................... H01N 59/16; H01N 55/02
[52] U.S. Cl. .......................... 504/151; 504/152; 504/120
[58] Field of Search ...................................... 504/151, 152

[56] References Cited

U.S. PATENT DOCUMENTS

| | | | |
|---|---|---|---|
| 4,654,208 | 3/1987 | Stockel et al. | 424/78 |
| 4,788,038 | 11/1988 | Matsunaga | 422/22 |
| 4,830,657 | 5/1989 | Jakubowski et al. | 71/67 |
| 5,098,472 | 3/1992 | Watkins et al. | 106/15.05 |
| 5,142,058 | 8/1992 | Willingham et al. | 548/213 |
| 5,160,527 | 11/1992 | Law et al. | 71/67 |
| 5,223,149 | 6/1993 | Antelman | 210/764 |
| 5,242,893 | 9/1993 | Willingham | 504/138 |
| 5,254,526 | 10/1993 | Hamilton | 504/119 |
| 5,290,601 | 3/1994 | Brooks et al. | 427/412.4 |
| 5,302,192 | 4/1994 | McLearie et al. | 106/18.33 |

*Primary Examiner*—Allen J. Robinson
*Assistant Examiner*—B. Bembenick
*Attorney, Agent, or Firm*—Brian S. Steinberger

[57] ABSTRACT

Mixtures that use photoactive agents that inhibit the growth of algae are disclosed. The agents include concentrations of approximately at least 5% to approximately 50% $TiO_2$, $WO_3$, $PtWO_3$—Pt—$WO_3$, or Pt—$TiO_2$. The agents can be combined together, and/or each agent can be combined with various coatings such as but not limited to a cement or a polymer binder. The coatings and agents can be applyed to surfaces that are exposed to water such as but not limited to an aquarium, liners on the inner walls of swimming pools, drinking water tanks and the like. Further, applications can include using the novel surfacing agent as part of a solar water heater for both a home and a pool, wherein in the latter application the heater is connected between pool pumps and the pool so that when light is absorbed inside the heater, the surfacing agent becomes active for inhibiting the growth of algae. The photoactive agent can also be applied as a non-toxic algae-retardant marine paint.

15 Claims, 6 Drawing Sheets

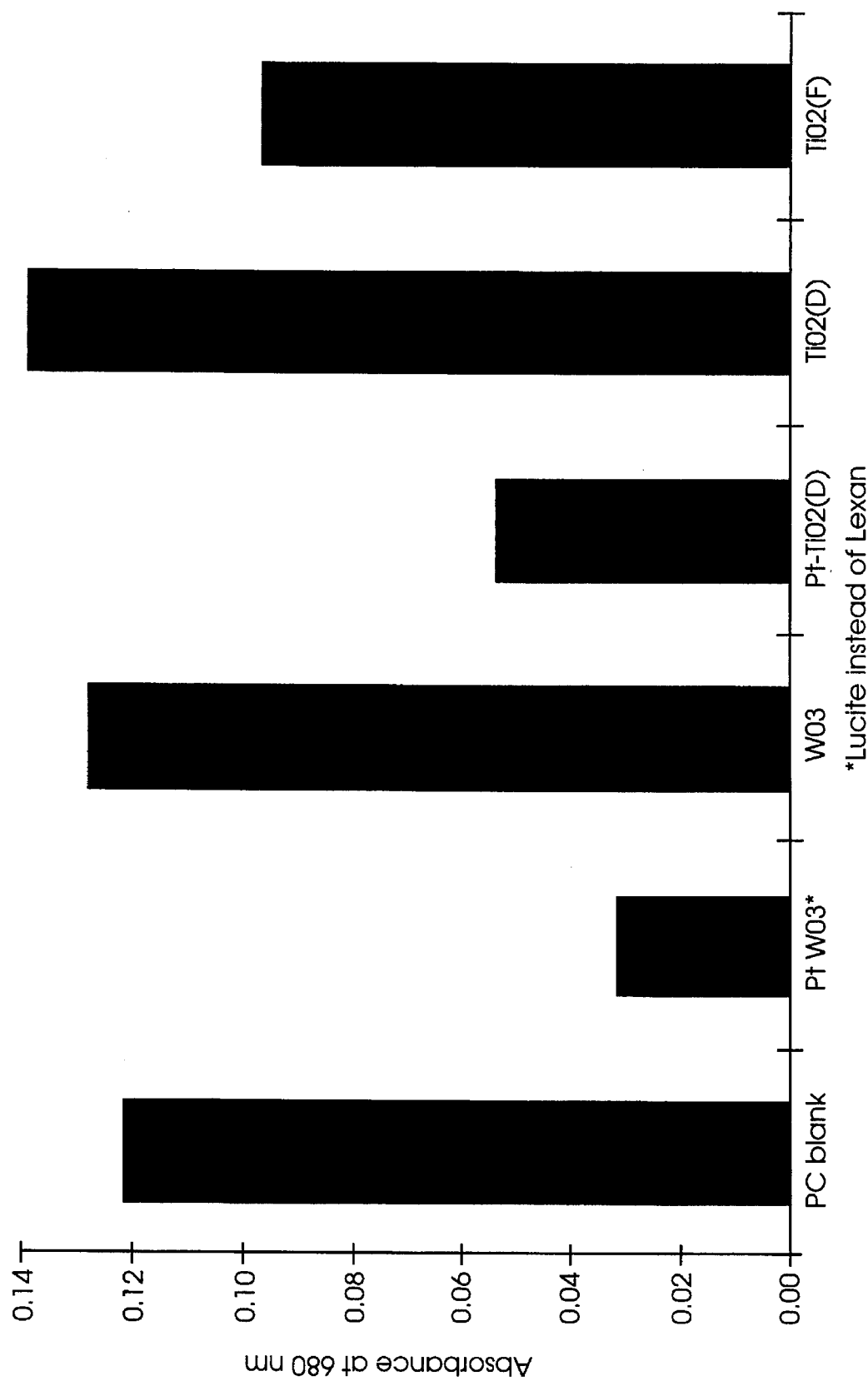

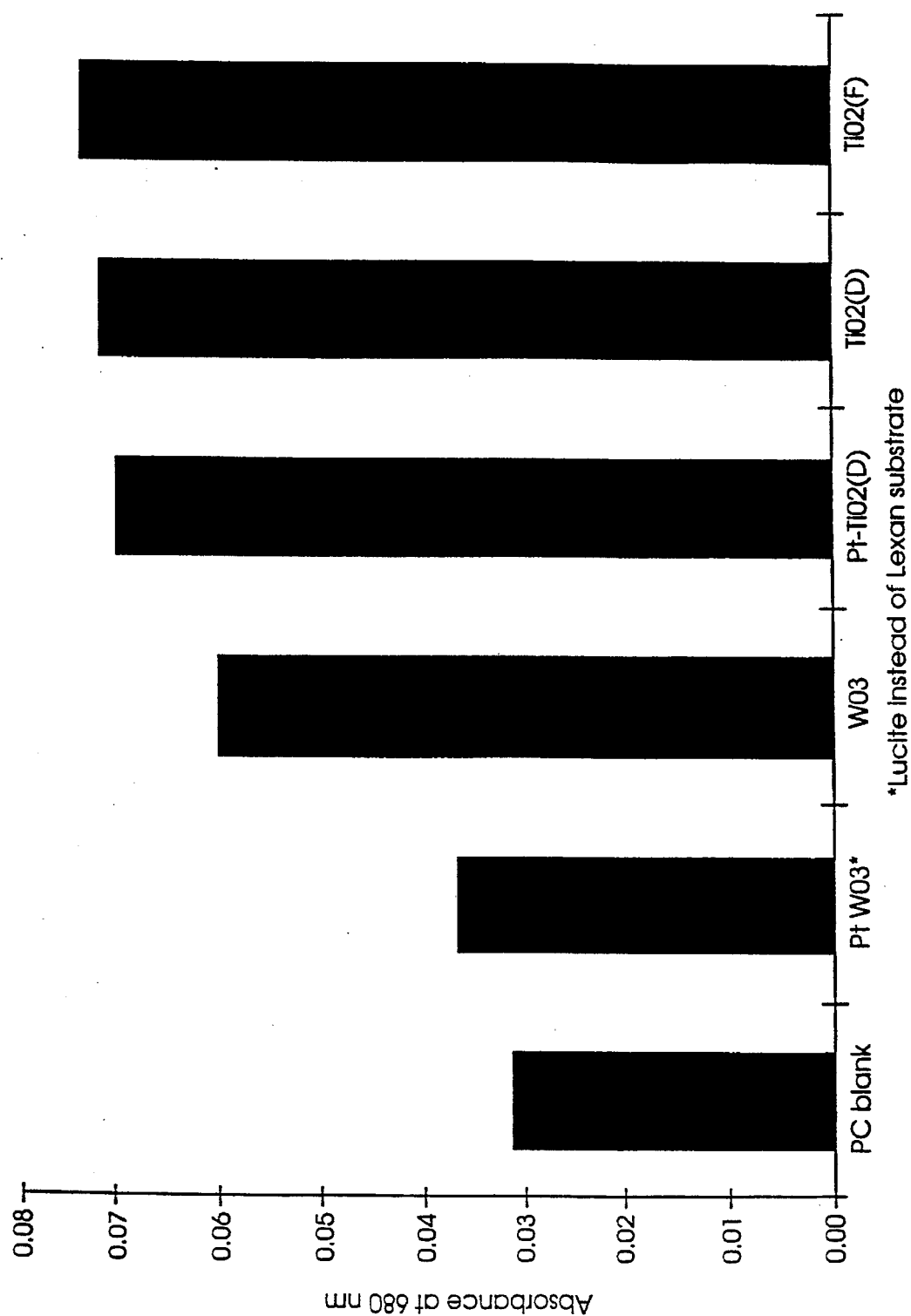

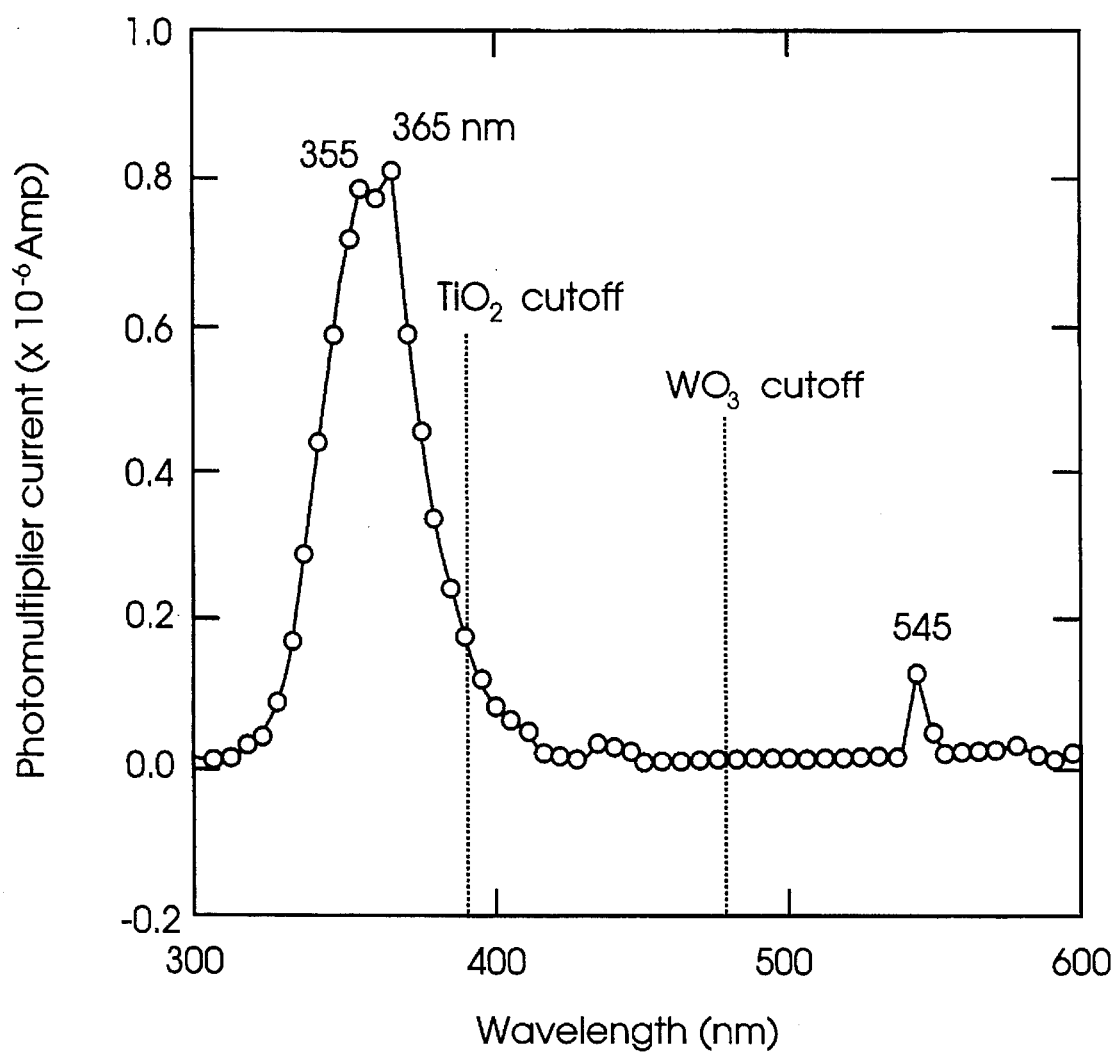
Figure 3. Spectral output of WKO black light

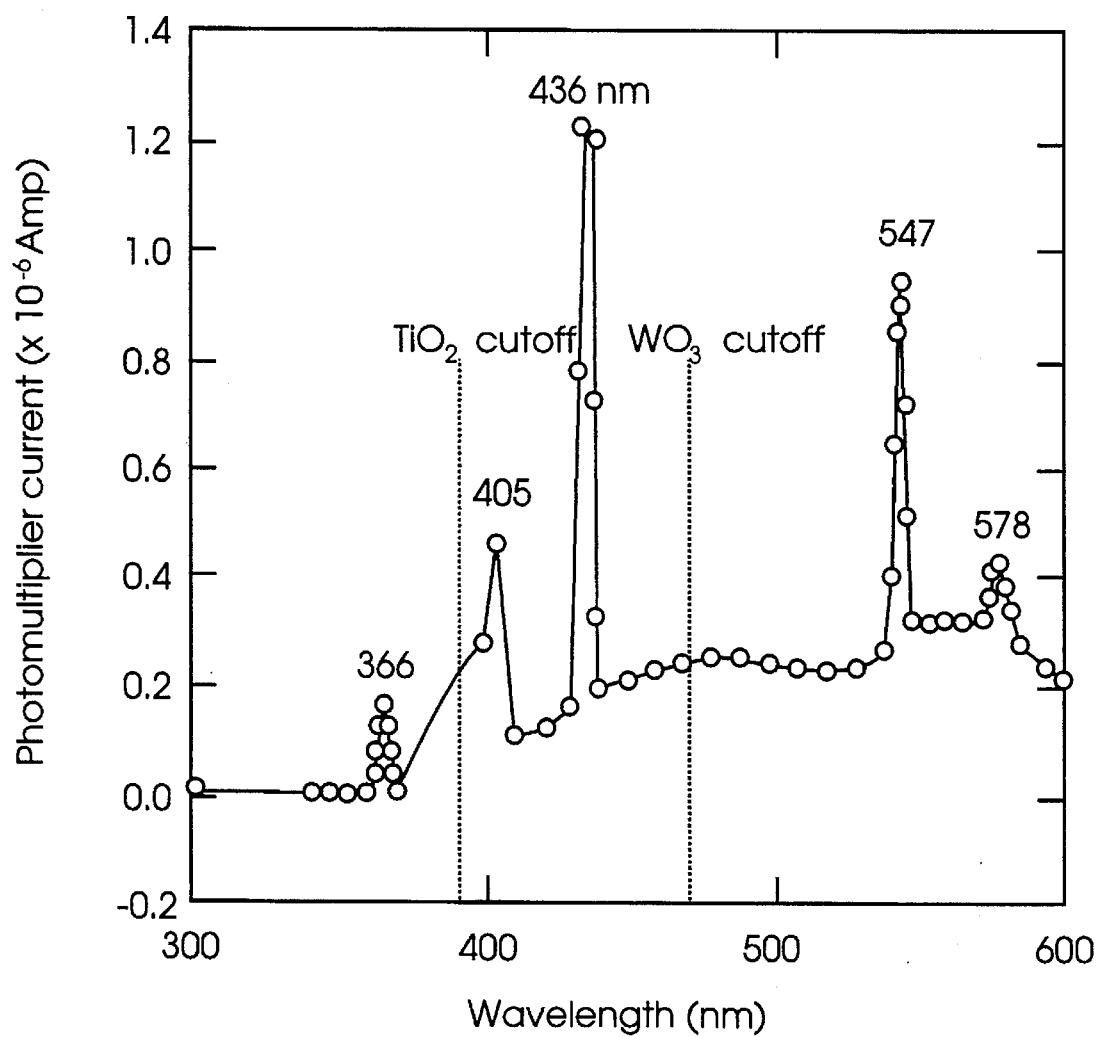
Figure 4. Spectral output of fluorescent light

Figure 5. Acrylic Flat - 13 Days
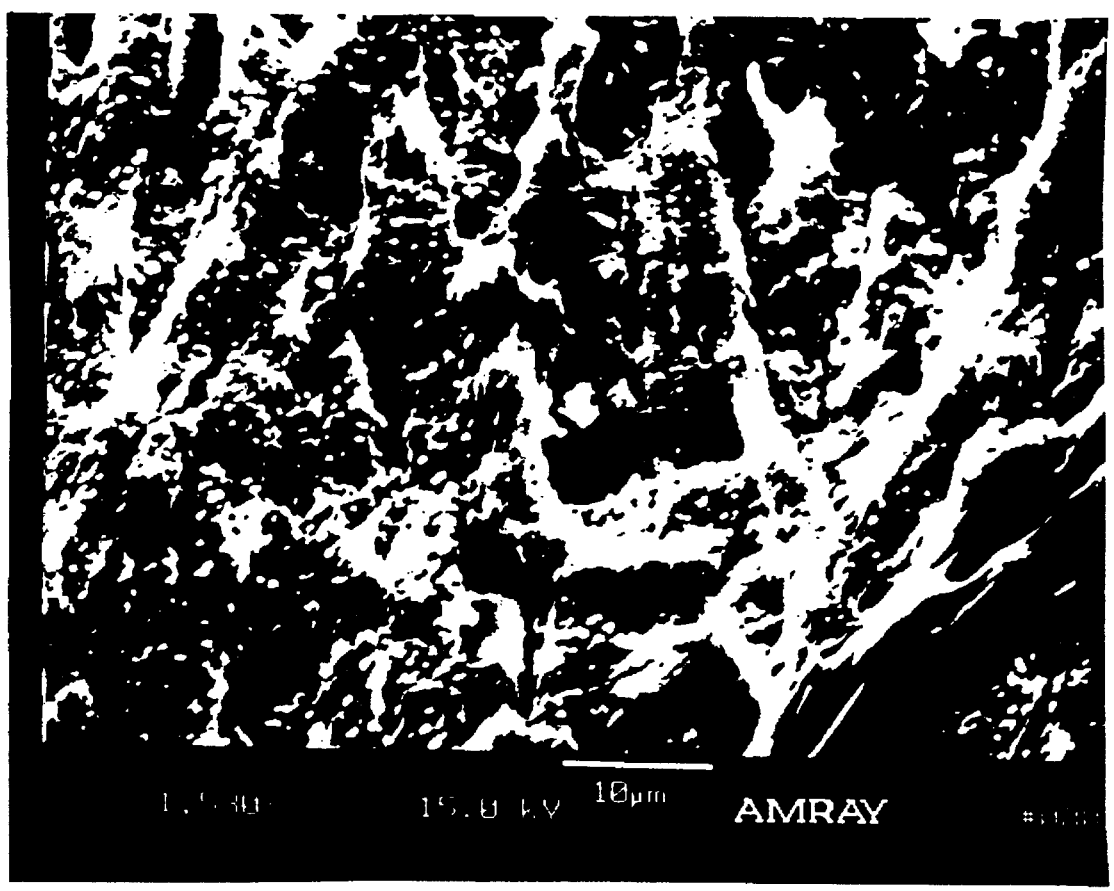

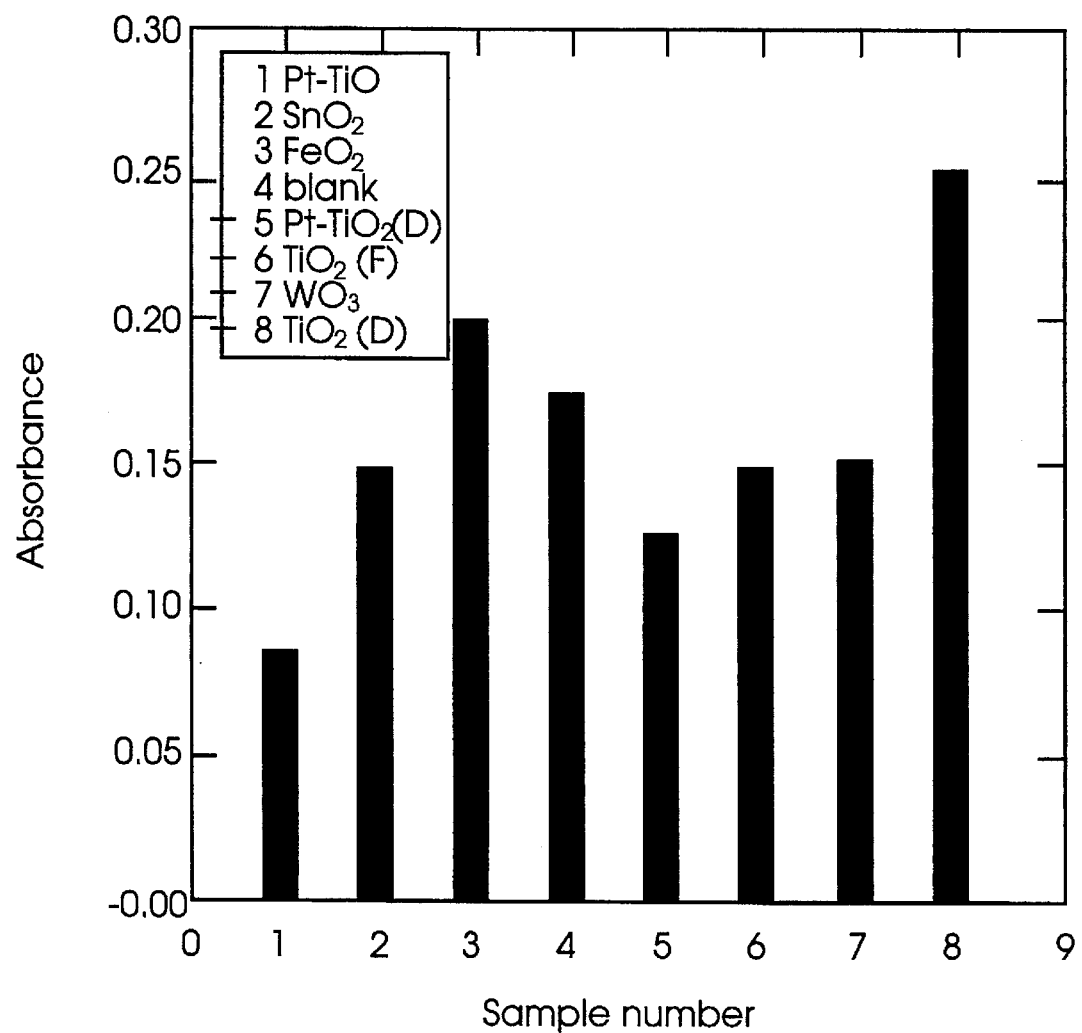
Figure 6. Bar Graph of Relative Growth Rates of Algae on Various Substrates

PHOTOCATALYTIC SURFACING AGENTS FOR INHIBITING ALGAE GROWTH

This invention relates to inhibiting the growth of fresh water and sea water plant life, and in particular to photocatalytic surfacing agents such as titanium dioxide and tungsten dioxide and methods of applying these agents to inhibit the growth of algae type plants.

BACKGROUND AND PRIOR ART

Undesirable plant growth such as algae has been a common problem for surfaces in both fresh water and seawater areas. For example, swimming pools, fountains and other manmade vessels that hold water are subject to fouling by algae.

Past methods for preventing algae have had numerous problems. Current surfacing agents for treating algae growth are basically toxins that also can be toxic to humans above threshold concentrations. For example, tributyl tin has been shown to be an effective toxin and has been incorporated into marine based paints for the hulls of boats. While gradual release of the toxin when the boat is underway is considered acceptable, a boat in port can generate unacceptable concentrations of toxin.

Certain preparations of Titanium Dioxide can be bright white in color, and are often used in commercial paint formulations. See U.S. Pat. No. 5,142,058. However, these preparations are made deliberately so as to be photo-inactive where any form of photo-activity is regarded as a negative characteristic, because the organic binder containing the pigment can be ultimately attacked and destroyed.

A standard toxin agent includes chlorine. Chlorine is a standard means for disinfecting swimming pool water and drinking water. However, disinfectants such as chlorine become spent and must be replaced over time with repetitive additional costs.

Toxin release agents are not only inferior due to their health effects on higher order plants and animals, but also because they represent a consumable item that must be eventually replaced.

Many types of algicides function as light blockers, absorbing the light necessary for algae growth. This involves dissolving one or more dyes in the water whose net absorption spectrum matches that of the algae. Thus, the water is dyed with an unnatural shade of blue or green that can be aesthetically unappealing. These algacides are also subject to eventual decomposition and require periodic replenishment.

SUMMARY OF THE INVENTION

The first objective of the present invention is to provide a surfacing agent for inhibiting algae growth.

The second object of this invention is to provide a method for inhibiting the growth of algae that is nontoxic to humans.

The third object of this invention is to provide a method for inhibiting the growth of algae that is photocatalytic and becomes active with light.

The fourth object of this invention is to provide a method for inhibiting the growth of algae that can remain active indefinitely over-time whenever light is available.

The fifth object of this invention is to provide a method for inhibiting the growth of algae that does not need constant replacement nor replenishment to remain active.

The sixth object of this invention is to provide a method of inhibiting the growth of algae without having to artificially color the water with algicidal dyes.

The seventh object of this invention is to provide an economical one-time cost for controlling the growth of algae.

Preferred embodiments of mixtures that combine photoactive agents along with surface coatings together inhibit the growth of algae when light is applied. The mixtures can include concentrations of an agent selected from approximately at least 5 % to approximately 50% $TiO_2$, $WO_3$, Pt—$WO_3$, or Pt—$TiO_2$. The agent can be with each other and/or further combined with various coatings such as but not limited to a cement or a polymer binder. The coatings and agents can be applyed to surfaces that are exposed to water such as but not limited to an aquarium, liners on the inner walls of swimming pools and the like. Further, applications can include using the novel surfacing agent as part of a solar water heater for both a home and a pool, wherein in the latter application the heater is connected between pool pumps and the pool so that when light is absorbed inside the heater, the surfacing agent becomes active for inhibiting the growth of algae. The photoactive agent can also be applied as a non-toxic algae-retardant marine paint.

Further objects and advantages of this invention will be apparent from the following detailed description of a presently preferred embodiment which is illustrated schematically in the accompanying drawings.

BRIEF DESCRIPTION OF THE FIGURES

FIG. 1 shows a graph representation of Algal growth on plastic substrates coated with various photocatalyst preparations by measuring the absorbance at 680 nm using a mixed lamp system combination of black and fluorescent lamps after seven days.

FIG. 2 shows a graph representation of Algal growth on photocatalyst preparations by measuring the absorbance at 680 nm using a fluorescent lamp after six days.

FIG. 3 shows a Spectral Output graph of WKO black light.

FIG. 4 shows a Spectral Output graph of fluorescent light.

FIG. 5 shows a picture of acrylic flat after 13 days which shows that the substrate without the photocatalytic coating under test conditions, will be completely covered with algae.

FIG. 6 shows a bar graph representing the relative growth rates of Algae by measuring at 680 nm for 8 different preparations.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Testing of various samples by photocatalytic means and their results occur in FIGS. 1 through 6. Photocatalytic means is used for enhancing the reaction rate within a chemical system when the system is irradiated with light.

FIG. 1 shows a graph representation of Algal growth on plastic substrates coated with various photocatalyst preparations by measuring the absorbance at 680 nm using a mixed lamp system combination of black and fluorescent lamps after seven days. Algae growth is inhibited when semiconductors were irradiated with combination dark and fluorescent lights. The shorter bars signify less algae growth than the larger bars.

Referring to FIG. 1, PC Blank refers to a bare polycarbonate plastic substrate. Pt—$WO_3$* is platinum and $WO_3$ is tungsten oxide. Pt—$TiO_2$ refers to platinized titanium dioxide. $TiO_2$ (D) is titanium dioxide from the Degussa Corporation, and $TiO_2$ (F) is from Fisher Scientific Company.

Under conditions conducive to algae growth, clean surfaces coated with photocatalytic agents will resist the spread of algae onto themselves.

FIG. 2 shows a graph representation of Algal growth on photocatalyst preparations by measuring the absorbance at 680 nm using a fluorescent lamp after six days. The taller bars signify that more algae growth has occurred. Thus, the photocatalysts failed to inhibit algae. The reason is that they could not make effective use of the fluorescent light spectral output.

FIG. 3 shows a Spectral Output graph of WKO black light in a plot of intensity versus wavelength. $TiO_2$ cutoff and $WO_3$ cutoff signify that the materials can only absorb light below their "cutoff" wavelength. This is a characteristic of their solid state electronic structure.

FIG. 4 shows a Spectral Output graph of fluorescent light in a plot of intensity versus wavelength. FIG. 5 shows a picture of acrylic flat after 13 days.

FIG. 6 shows a bar graph representing the relative growth rates of Algae by measuring at 680 nm for 8 different preparations.

From the testing that has occurred as represented in FIGS. 1–6, algae inhibition can occur as low as 5% by weight for $TiO_2$ and $WO_3$. Surface coatings of <1 mm thickness may need 40 to 50% $TiO_2$ and $WO_3$, of which 0.5% can include other materials such as platinum. Other surface coatings and mixtures that can be included with $TiO_2$ and $WO_3$, include polymers such as polymethyl methacrylate, polycarbonate and white portland cement. $TiO_2$ and $WO_3$ can be blended together with types of cement and water according to cement vendor's instructions. $TiO_2$ and $WO_3$ can be blended together with types of polymers by applying a pure polymer coating then softening with solvents such as dichloroethane and feathering the photoactive powder into the surface.

The various photoactive surfacing agents disclosed above can be mixed together and used without reducing the performance of the individual components. Furthermore a potential synergistic effect can be realized when combining together agents such as but not limited to $TiO_2$ and $WO_3$ together in one mixture.

The surfacing agents can be used in applications such as but not limited to non-toxic algaeretardant marine paint, surfacing agents on light-stricken walls in an aquarium, surfacing agent for lining the inner walls of swimming pools and the like. Further, applications can include using the novel surfacing agent as part of a solar water heater for either or both a home and a pool. In a pool application, the surfacing agent is applied to an inner wall within the heater that is connected between pool pumps and the pool so that when light is absorbed inside the heater, the surfacing agent becomes active for inhibiting the growth of algae.

Although the invention has been described as being used to inhibit the growth of algae, the invention can be used as a bacterial control for disinfection of water for drinking or bathing.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of inhibiting the growth of algae on surfaces that are exposed to water comprising the steps of:

applying a mixture of a coating combined with $WO_3$ to a water exposed surface; and applying light to the mixture which becomes photoactive to inhibit growth of algae.

2. The method of inhibiting the growth of algae of claim 1, wherein the coating includes:

a polymer binder.

3. The method of inhibiting the growth of algae of claim 1, wherein the coating includes:

a cement.

4. A method of inhibiting the growth of algae on surfaces that are exposed to water using a photoactive coating comprising the steps of:

applying a coating combined with a photoactive agent that includes
Pt—$TiO_2$, to a water exposed surface; and applying light to the coating and the agent which inhibits the growth of algae on the surface.

5. The method of inhibiting the growth of algae of claim 4, wherein the coating includes:

a polymer binder.

6. The method of inhibiting the growth of algae of claim 4, wherein the coating includes:

a cement.

7. The method of inhibiting the growth of algae of claim 4, wherein the agent further includes:

Pt—$WO_3$.

8. The method of inhibiting the growth of algae of claim 4, wherein the agent includes:

at least 5% by weight photoactive agent.

9. The method of inhibiting the growth of algae of claim 4, wherein the agent includes:

at least 50% by weight photoactive agent.

10. The method of inhibiting the growth of algae of claim 4, wherein the surface includes:

an inner wall within an aquarium.

11. The method of inhibiting the growth of algae of claim 4, wherein the surface includes:

an inner wall of a swimming pool.

12. The method of inhibiting the growth of algae of claim 4, wherein the surface includes:

an inner wall within a solar water heater.

13. A method of inhibiting the growth of algae on surfaces that are exposed to water using a photoactive coating comprising the steps of:

applying a coating combined with a photoactive agent that includes
Pt—$WO_3$, to a water exposed surface; and applying light to the coating and the agent which inhibits the growth of algae on the surface.

14. The method of inhibiting the growth of algae of claim 13, wherein the coating includes:

a polymer binder.

15. The method of inhibiting the growth of algae of claim 13, wherein the coating includes:

a cement.

* * * * *